US011690680B2

(12) United States Patent
Montane et al.

(10) Patent No.: US 11,690,680 B2
(45) Date of Patent: Jul. 4, 2023

(54) TRACKABLE PROTECTIVE PACKAGING FOR TOOLS AND METHODS FOR CALIBRATING TOOL INSTALLATION USING THE SAME

(71) Applicant: MAKO Surgical Corp., Ft. Lauderdale, FL (US)

(72) Inventors: Roberto Montane, Lake Worth, FL (US); Brandt Williams, Plantation, FL (US); Seamus Gilhooley, Galway (IE); Jonathan Mark Morgan, Biscayne Park, FL (US); Mark Palm, Davie, FL (US); Michael Vu, Sunrise, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 500 days.

(21) Appl. No.: 16/817,118

(22) Filed: Mar. 12, 2020

(65) Prior Publication Data

US 2020/0297429 A1 Sep. 24, 2020

Related U.S. Application Data

(60) Provisional application No. 62/820,577, filed on Mar. 19, 2019.

(51) Int. Cl.
*A61B 34/20* (2016.01)
*A61B 34/30* (2016.01)
(Continued)

(52) U.S. Cl.
CPC .............. *A61B 34/20* (2016.02); *A61B 34/10* (2016.02); *A61B 34/30* (2016.02); *A61B 34/70* (2016.02);
(Continued)

(58) Field of Classification Search
None
See application file for complete search history.

(56) References Cited

U.S. PATENT DOCUMENTS

| 3,495,702 A | 2/1970 | Kuster |
| 4,519,501 A | 5/1985 | Cerwin |

(Continued)

FOREIGN PATENT DOCUMENTS

| EP | 2298652 A1 | 3/2011 |
| EP | 2292528 B1 | 2/2013 |

(Continued)

OTHER PUBLICATIONS

English language abstract for EP 2 292 528 extracted from espacenet.com database on Apr. 30, 2020, 1 pages.

(Continued)

*Primary Examiner* — Tamara L Weber
(74) *Attorney, Agent, or Firm* — Howard & Howard Attorneys PLLC

(57) ABSTRACT

Protective packaging, surgical kits, systems, and methods are described herein for assisting in determining whether a tool is properly installed on a surgical device. The protective packaging retains the tool and has trackable features defined relative to a tool center point of the tool. The trackable features have a predetermined state defined relative to the tool center point and the trackable features are configured to be detectable by a localizer to locate the tool center point. One or more controllers can compare the actual state of the tool center point with an expected state of the tool center point, which is based on an expected condition in which the tool is properly mounted to the surgical device. Based on the comparison, the one or more controllers can determine whether the tool is properly mounted to the surgical device.

12 Claims, 4 Drawing Sheets

(51) Int. Cl.
*A61B 34/10* (2016.01)
*A61B 34/00* (2016.01)

(52) U.S. Cl.
CPC ... *A61B 2034/104* (2016.02); *A61B 2034/107* (2016.02); *A61B 2034/2057* (2016.02); *A61B 2034/2065* (2016.02)

(56) References Cited

U.S. PATENT DOCUMENTS

| | | | |
|---|---|---|---|
| 5,220,769 A | 6/1993 | Brown et al. | |
| 5,246,109 A | 9/1993 | Markle et al. | |
| 5,392,917 A | 2/1995 | Alpern et al. | |
| 5,485,917 A | 1/1996 | Early | |
| 5,542,427 A | 8/1996 | Aekerfeldt | |
| 5,542,539 A | 8/1996 | Early | |
| 5,584,164 A | 12/1996 | Sinn | |
| 5,727,682 A | 3/1998 | Abidin et al. | |
| 5,727,685 A | 3/1998 | Laganza et al. | |
| 5,842,567 A | 12/1998 | Rowe et al. | |
| 5,921,992 A | 7/1999 | Costales et al. | |
| 5,947,288 A | 9/1999 | Dykstra et al. | |
| 5,987,960 A | 11/1999 | Messner et al. | |
| 6,059,111 A | 5/2000 | Davila et al. | |
| 6,059,112 A | 5/2000 | Dykstra et al. | |
| 6,161,695 A | 12/2000 | Nicolais | |
| 6,332,891 B1 | 12/2001 | Himes | |
| 6,340,363 B1 | 1/2002 | Bolger et al. | |
| 6,412,639 B1 | 7/2002 | Hickey | |
| 6,511,418 B2 | 1/2003 | Shahidi et al. | |
| 6,517,478 B2 | 2/2003 | Khadem | |
| 6,671,058 B1 | 12/2003 | Braunecker et al. | |
| 6,814,236 B2 | 11/2004 | Roshdy | |
| 6,837,027 B2 | 1/2005 | Hickey | |
| 6,866,671 B2 | 3/2005 | Tierney et al. | |
| 6,915,901 B2 | 7/2005 | Feinberg et al. | |
| 6,996,487 B2 | 2/2006 | Jutras et al. | |
| 7,043,961 B2 | 5/2006 | Pandey et al. | |
| 7,104,401 B2 | 9/2006 | Smith et al. | |
| 7,128,208 B2 | 10/2006 | Hull | |
| 7,166,114 B2 | 1/2007 | Moctezuma De La Barrera et al. | |
| 7,316,318 B1 | 1/2008 | Rosten et al. | |
| 7,320,404 B2 | 1/2008 | Landis | |
| 7,331,463 B2 | 2/2008 | Hickey | |
| 7,353,946 B2 | 4/2008 | Cervantes | |
| 7,451,870 B2 | 11/2008 | Donahoe et al. | |
| 7,467,710 B2 | 12/2008 | Cerwin et al. | |
| 7,516,845 B2 | 4/2009 | Lang et al. | |
| 7,611,008 B2 | 11/2009 | Ruffieux et al. | |
| 7,617,932 B2 | 11/2009 | Windus-Smith et al. | |
| 7,621,395 B2 | 11/2009 | Mogensen et al. | |
| 7,648,030 B2 | 1/2010 | Landis | |
| 7,726,564 B2 | 6/2010 | Goldbach | |
| 7,770,722 B2 | 8/2010 | Donahoe et al. | |
| 7,770,728 B2 | 8/2010 | Kærn | |
| 7,820,446 B2 * | 10/2010 | Feilkas | A61B 50/30 422/50 |
| 7,962,192 B2 | 6/2011 | Bodduluri et al. | |
| 7,975,842 B2 | 7/2011 | Thoes et al. | |
| 8,006,839 B2 | 8/2011 | Hafner | |
| 8,010,180 B2 | 8/2011 | Quaid et al. | |
| 8,020,703 B2 | 9/2011 | List et al. | |
| 8,042,689 B2 | 10/2011 | Frojd et al. | |
| D655,165 S | 3/2012 | Jensen et al. | |
| 8,146,329 B2 | 4/2012 | Bryant et al. | |
| 8,172,866 B2 | 5/2012 | List | |
| 8,261,910 B2 | 9/2012 | Guenter et al. | |
| 8,303,599 B2 | 11/2012 | Hess et al. | |
| 8,320,612 B2 | 11/2012 | Knobel et al. | |
| 8,365,910 B2 | 2/2013 | Valaie et al. | |
| 8,517,174 B2 | 8/2013 | Dacey et al. | |
| 8,739,801 B2 | 6/2014 | Rains et al. | |
| 8,770,405 B2 | 7/2014 | Dacey et al. | |
| 8,838,205 B2 | 9/2014 | Shoham et al. | |
| 8,881,900 B2 | 11/2014 | Witt et al. | |
| 8,893,883 B2 | 11/2014 | Valaie et al. | |
| D731,326 S | 6/2015 | Johansson | |
| 9,068,820 B2 | 6/2015 | Kosmecki et al. | |
| 9,096,368 B2 | 8/2015 | Wu | |
| 9,119,655 B2 | 9/2015 | Bowling et al. | |
| 9,138,296 B2 | 9/2015 | Grabowski | |
| 9,157,762 B2 | 10/2015 | Ji | |
| 9,265,579 B2 | 2/2016 | Richart | |
| 9,393,039 B2 | 7/2016 | Lechner et al. | |
| 9,439,658 B2 * | 9/2016 | Ford | A61B 17/1757 |
| 9,474,686 B2 | 10/2016 | Neal et al. | |
| 9,532,847 B2 | 1/2017 | Hendrickson et al. | |
| 9,585,727 B2 | 3/2017 | Richart | |
| 9,592,098 B2 | 3/2017 | Richart | |
| 9,597,092 B2 | 3/2017 | Pernot et al. | |
| RE46,409 E | 5/2017 | Foley et al. | |
| 9,652,591 B2 * | 5/2017 | Moctezuma de la Barrera | A61B 17/154 |
| 9,707,039 B2 | 7/2017 | Grabowski et al. | |
| 9,717,843 B2 | 8/2017 | Grucela et al. | |
| 9,750,579 B2 | 9/2017 | Richart | |
| 9,775,626 B2 | 10/2017 | Revie et al. | |
| 9,776,783 B2 | 10/2017 | Nadig et al. | |
| 9,828,157 B2 | 11/2017 | Roesler | |
| D806,541 S | 1/2018 | Love et al. | |
| 9,872,754 B2 | 1/2018 | Tuechsen et al. | |
| 9,926,116 B2 | 3/2018 | Kinyon | |
| D818,813 S | 5/2018 | Love et al. | |
| 9,975,679 B2 | 5/2018 | Hulliger | |
| 9,999,469 B2 | 6/2018 | Roesler | |
| 10,004,567 B2 | 6/2018 | Dacey et al. | |
| 10,016,247 B2 | 7/2018 | Grabowski et al. | |
| 10,017,303 B2 | 7/2018 | Wagner et al. | |
| 10,029,043 B2 | 7/2018 | Grucela et al. | |
| 10,059,499 B2 | 8/2018 | Roesler et al. | |
| 10,086,131 B2 | 10/2018 | Okihara | |
| 10,130,439 B2 | 11/2018 | Richart | |
| 10,159,555 B2 | 12/2018 | Bailly et al. | |
| 10,357,184 B2 | 7/2019 | Crawford et al. | |
| 10,456,207 B2 | 10/2019 | Flatt | |
| 10,556,345 B2 | 2/2020 | Kamikawa et al. | |
| 2002/0032452 A1 | 3/2002 | Tierney et al. | |
| 2003/0195526 A1 | 10/2003 | Vilsmeier | |
| 2005/0187562 A1 | 8/2005 | Grimm et al. | |
| 2005/0218024 A1 | 10/2005 | Lang et al. | |
| 2005/0220849 A1 | 10/2005 | Hickey | |
| 2005/0288575 A1 * | 12/2005 | de la Barrera | A61B 34/20 600/423 |
| 2006/0142657 A1 | 6/2006 | Quaid et al. | |
| 2006/0200046 A1 | 9/2006 | Windus-Smith et al. | |
| 2007/0185486 A1 | 8/2007 | Hauck et al. | |
| 2007/0203393 A1 | 8/2007 | Stefanchik | |
| 2007/0295620 A1 | 12/2007 | Collet et al. | |
| 2008/0004633 A1 * | 1/2008 | Arata | A61B 34/20 606/130 |
| 2008/0228195 A1 | 9/2008 | von Jako et al. | |
| 2009/0163930 A1 | 6/2009 | Aoude et al. | |
| 2009/0247861 A1 | 10/2009 | Manus et al. | |
| 2011/0264107 A1 * | 10/2011 | Nikou | A61B 17/1633 700/258 |
| 2012/0305427 A1 | 12/2012 | Felder et al. | |
| 2013/0299371 A1 | 11/2013 | Johansson | |
| 2014/0148808 A1 | 5/2014 | Inkpen et al. | |
| 2014/0251845 A1 | 9/2014 | Roesler | |
| 2014/0251846 A1 | 9/2014 | Roesler | |
| 2015/0182293 A1 | 7/2015 | Yang et al. | |
| 2015/0297296 A1 | 10/2015 | Stauder et al. | |
| 2016/0135895 A1 | 5/2016 | Faasse et al. | |
| 2016/0151119 A1 | 6/2016 | Michel et al. | |
| 2016/0166350 A1 | 6/2016 | Burkhardt et al. | |
| 2016/0244234 A1 | 8/2016 | Mayer et al. | |
| 2016/0249986 A1 | 9/2016 | Kruger et al. | |
| 2017/0000583 A1 | 1/2017 | Lechner et al. | |
| 2017/0007388 A1 | 1/2017 | Neal et al. | |
| 2017/0119487 A1 | 5/2017 | Binder et al. | |
| 2017/0137194 A1 | 5/2017 | Lorence | |
| 2017/0143432 A1 | 5/2017 | Bowling et al. | |
| 2017/0252109 A1 | 9/2017 | Yang et al. | |
| 2017/0290634 A1 | 10/2017 | Dacey | |
| 2017/0333052 A1 | 11/2017 | Ding et al. | |

(56) References Cited

U.S. PATENT DOCUMENTS

| | | |
|---|---|---|
| 2017/0333138 A1 | 11/2017 | Arata et al. |
| 2017/0349347 A1 | 12/2017 | Bentz |
| 2017/0355505 A1 | 12/2017 | Nadig et al. |
| 2018/0014888 A1 | 1/2018 | Bonny et al. |
| 2018/0023946 A1* | 1/2018 | Elliot .................. B25J 9/1692 |
| | | 356/614 |
| 2018/0140223 A1 | 5/2018 | Kheradpir et al. |
| 2018/0162619 A1 | 6/2018 | Kocur et al. |
| 2018/0168750 A1 | 6/2018 | Staunton et al. |
| 2018/0214167 A1 | 8/2018 | Overmyer et al. |
| 2018/0222655 A1 | 8/2018 | Grabowski et al. |
| 2018/0235348 A1 | 8/2018 | Booker |
| 2018/0296293 A1 | 10/2018 | Ueda |
| 2018/0296297 A1 | 10/2018 | Moloney et al. |
| 2018/0296749 A1 | 10/2018 | Grucela et al. |
| 2018/0311008 A1 | 11/2018 | Grabowski et al. |
| 2018/0344422 A1 | 12/2018 | Deck |
| 2019/0001050 A1 | 1/2019 | Okihara |
| 2019/0070019 A1 | 3/2019 | Frederick et al. |
| 2019/0269465 A1 | 9/2019 | Murrell et al. |
| 2019/0315563 A1 | 10/2019 | Johansson |
| 2020/0038115 A1 | 2/2020 | Schwamb et al. |
| 2020/0054199 A1 | 2/2020 | Kambe et al. |
| 2020/0121400 A1* | 4/2020 | Girardeau-Montaut ................... |
| | | A61B 34/20 |
| 2020/0261161 A1* | 8/2020 | Frielinghaus .......... A61B 34/20 |

FOREIGN PATENT DOCUMENTS

| | | |
|---|---|---|
| EP | 2662312 B1 | 10/2014 |
| WO | 2011135246 A2 | 11/2011 |
| WO | 2017087732 A1 | 5/2017 |
| WO | 2017114059 A1 | 7/2017 |
| WO | 2017129757 A1 | 8/2017 |
| WO | 2017157763 A1 | 9/2017 |
| WO | 2017176569 A1 | 10/2017 |
| WO | 2017185029 A1 | 10/2017 |
| WO | 2017185052 A1 | 10/2017 |
| WO | 2018011257 A1 | 1/2018 |
| WO | 2018052832 A1 | 3/2018 |
| WO | 2018106110 A1 | 6/2018 |
| WO | 2018112107 A1 | 6/2018 |
| WO | 2018156589 A2 | 8/2018 |
| WO | 2018156611 A1 | 8/2018 |
| WO | 2018164497 A1 | 9/2018 |
| WO | 2018198308 A1 | 11/2018 |
| WO | 2018202805 A1 | 11/2018 |
| WO | 2018227066 A1 | 12/2018 |
| WO | 2019227215 A1 | 12/2019 |

OTHER PUBLICATIONS

English language abstract for WO 2011/135246 extracted from espacenet.com database on Apr. 16, 2020, 2 pages.

English language abstract and machine-assisted English translation for WO 2017/114059 extracted from espacenet.com database on Apr. 16, 2020, 9 pages.

English language abstract and machine-assisted English translation for WO 2018/164497 extracted from espacenet.com database on Apr. 16, 2020, 15 pages.

English language abstract for WO 2018/198308 extracted from espacenet.com database on Apr. 16, 2020, 2 pages.

English language abstract and machine-assisted English translation for WO 2018/202805 extracted from espacenet.com database on Apr. 16, 2020, 14 pages.

International Search Report for Application No. PCT/US2018/027138 dated Jun. 25, 2018, 3 pages.

* cited by examiner

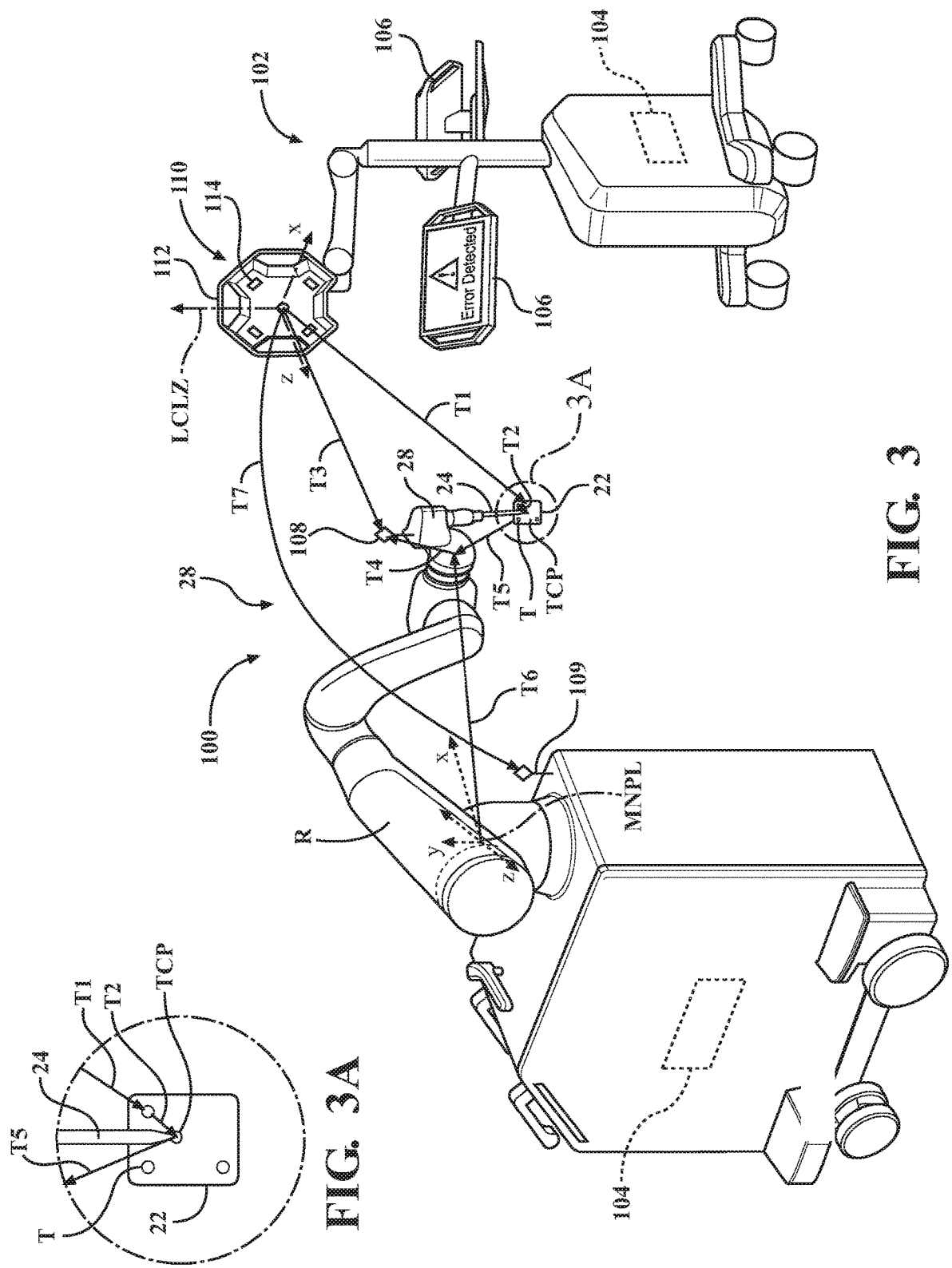

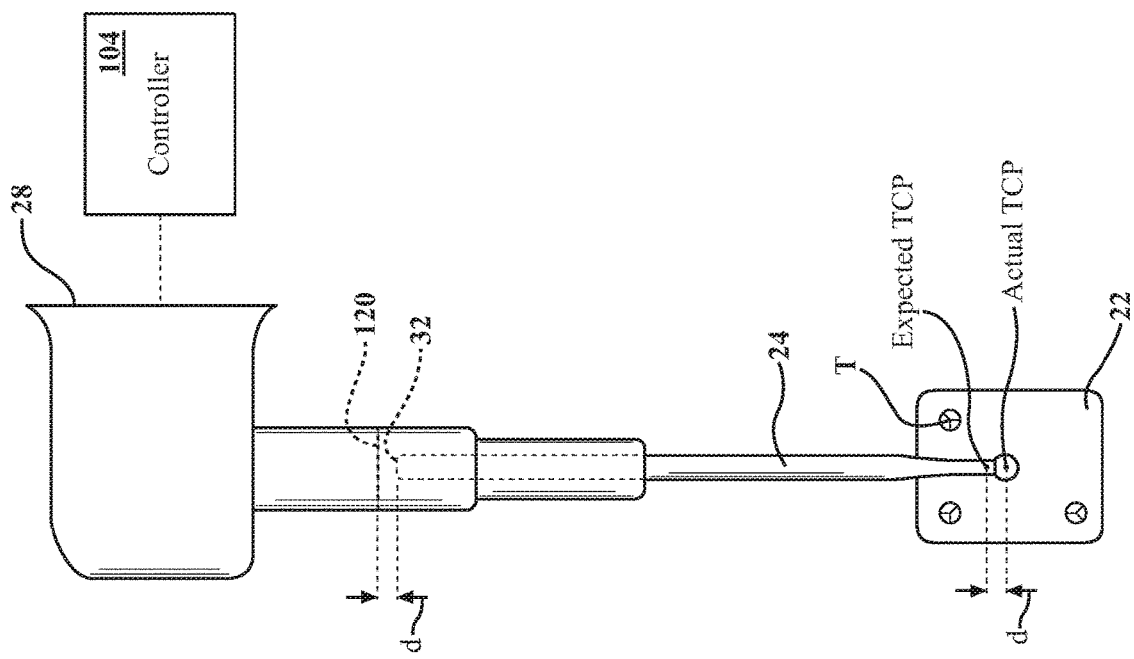
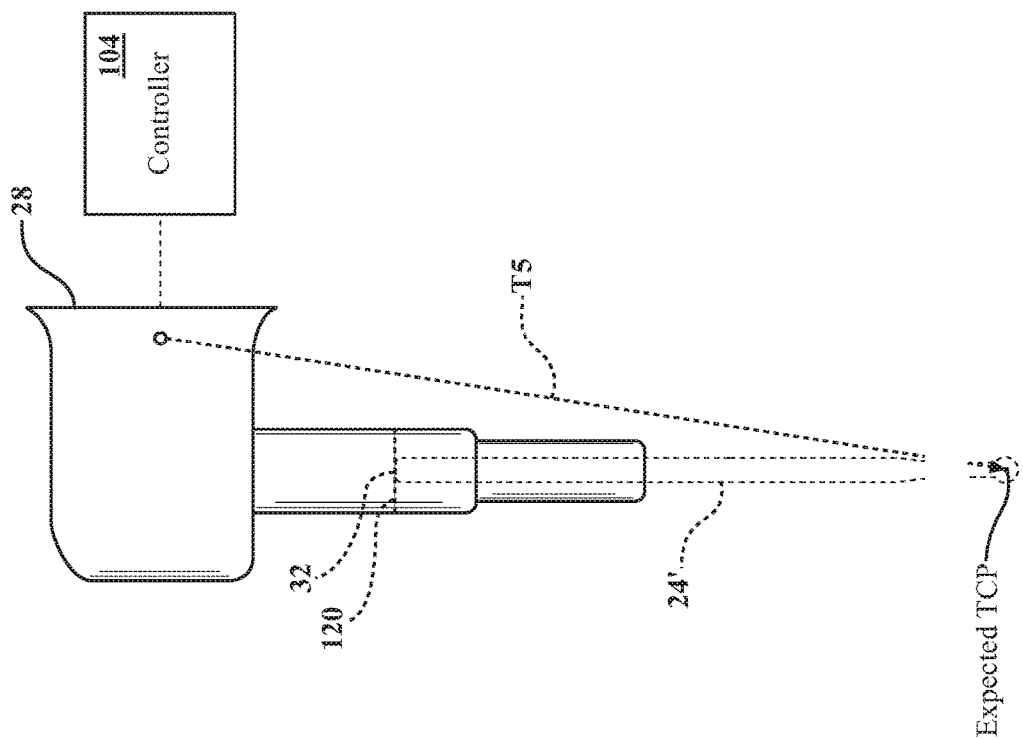

TRACKABLE PROTECTIVE PACKAGING FOR TOOLS AND METHODS FOR CALIBRATING TOOL INSTALLATION USING THE SAME

CROSS-REFERENCE TO RELATED APPLICATIONS

The subject application claims priority to and all the benefits of U.S. Provisional Patent Application No. 62/820,577, filed Mar. 19, 2019, the contents of which are hereby incorporated by reference in its entirety.

BACKGROUND

A surgical device, such as a robot, often receives a tool or instrument for use during a surgical procedure. The tool may be a cutting accessory, such as a saw, bur drill, having a head with sharp features configured to resect tissue such as bone. Exposed handling of the tool may result in surgical site infection, injury, and other undesirable consequences. For these reasons, such tools often require a type of protective packaging to prevent inadvertent exposure before and during installation.

A working portion of the tool (e.g., such as the burring portion) must be precisely known by the system in order to effect proper control of the surgical device. Navigation systems are often utilized with surgical systems to track surgical devices, the patient, and additional tools that may be utilized in the surgical procedure. The navigation system often utilizes markers or trackers that are attached to the objects that need to be tracked.

Tool accessories, such as those mentioned above, are interchangeably installed, often operate a high rate of movement and have high exposure to the surgical site thereby requiring sterilization. Therefore, markers or trackers on the tool may negatively affect physical performance of the tool or may be impossible to practically implement on the tool. Furthermore, markers on the tool would likely be destroyed during sterilization. For these reasons, such tool accessories are often not directly tracked by the navigation system.

In such situations, there may be no way of knowing whether the tool is properly installed to the surgical device. There may be situations where the tool appears to be properly installed to the operator, when in fact, the tool may be slightly (e.g., by a few millimeters) mis-aligned or not fully seated.

Prior techniques for confirming tool installation require additional instruments, such as tracked digitization devices, that are used to digitize certain points on the tool for calibration purposes. However, such techniques require additional tools and operator steps thereby increasing operating time and costs. Additionally, digitization techniques may produce measurements that are less accurate because the process requires manual operator involvement in digitizing. For example, the actual digitization point may deviate from the digitization point expected by the system.

Another prior method to assess installation accuracy is to use a custom end effector for a robotic system whereby the end effector has markers or tracking elements detectable by the navigation system and the tool accessory is already in a pre-installed, fixed position, relative to the end effector. In such instances, the robot must move to certain poses to implement a calibration process. In these poses, a kinematic location of the robot is known to the system and the locations of the tracking elements on the end effector are compared to the kinematic robot locations to assess accuracy. However, such methods are not suitable for end effectors that can accept different tools. Furthermore, the end effector must be customized with the given tool and therefore, this increases costs and complexity in end effector versions. Additionally, this technique requires the robot to assume certain poses, thereby increasing operating room time.

Techniques designed to overcome one or more of the aforementioned disadvantages are desired.

SUMMARY

In one example, a method for operating a system is provided, the system comprising a surgical device and a tool for mounting to the surgical device, the tool including a working portion having a tool center point, a protective packaging for retaining the working portion, the protective packaging comprising trackable features having a predetermined state defined relative to an actual state of the tool center point, one or more controllers configured to store the predetermined states of the trackable features and to store an expected state of the tool center point based on an expected condition in which the tool is properly mounted to the surgical device, and a localizer, the method comprising: detecting, with the localizer, actual states of the trackable features in a coordinate system; determining, with the one or more controllers, the actual state of the tool center point in the coordinate system based on the actual states of the trackable features detected by the localizer and the predetermined state of the trackable features defined relative to the actual state of the tool center point; comparing, with the one or more controllers, the actual state and expected state of the tool center point; and evaluating, with the one or more controllers, whether the tool is properly mounted to the surgical device based on comparing the actual state and expected state of the tool center point.

In another example, a system is provided. The system comprising: a surgical device; a tool configured to mount to the surgical device and comprising a working portion having a tool center point; a protective packaging configured to retain the working portion of the tool, the protective packaging comprising trackable features having a predetermined state defined relative to an actual state of the tool center point; one or more controllers coupled to the surgical device and configured to store the predetermined states of the trackable features and to store an expected state of the tool center point based on an expected condition in which the tool is properly mounted to the surgical device; and a localizer coupled to the one or more controllers and being configured to detect actual states of the trackable features in a coordinate system; and wherein the one or more controllers are configured to: determine the actual state of the tool center point in the coordinate system based on the actual states of the trackable features detected by the localizer and the predetermined state of the trackable features defined relative to the actual state of the tool center point; compare the actual state and expected state of the tool center point; and evaluate whether the tool is properly mounted to the surgical device based on comparing the actual state and expected state of the tool center point.

In another example, a protective packaging for a tool is provided, wherein the tool includes a working portion and a tool center point associated with the working portion, the protective packaging comprising: a distal section defining a cavity configured to retain the working portion; and the distal section comprising trackable features, wherein the trackable features have a predetermined state defined relative to a state of tool center point, and the trackable features are configured to be detectable by a localizer for enabling the localizer to locate the tool center point.

In another example, an assembly for a surgical procedure is provided, the assembly comprising: a tool including a working portion and a tool center point associated with the working portion; and a protective packaging that retains the working portion, and wherein the protective packaging comprises trackable features, wherein the trackable features have a predetermined state defined relative to the tool center point and the trackable features are configured to be detectable by a localizer for enabling the localizer to locate the tool center point.

BRIEF DESCRIPTION OF THE DRAWINGS

Advantages of the present disclosure will be readily appreciated as the same becomes better understood by reference to the following detailed description when considered in connection with the accompanying drawings wherein:

FIG. 3 is an example system comprising a navigation system utilized in conjunction with a surgical device, in this example, the end effector of a robotic manipulator which is configured to receive the tool retained by the packaging, and further illustrates relationships between components of the system that can be known or determinable by one or more controllers to determine the state of the tool center point of the tool.

FIG. 3A is an expanded view of the packaging and tool from FIG. 3 further illustrating the relationship between the trackable features and the tool center point.

FIG. 4 illustrates one example of surgical device and the one or more controllers wherein an expected tool center point of the tool known to the one or more controllers is illustrated in a hypothetical condition wherein the tool is properly installed to the surgical device.

FIG. 5 illustrates the surgical device of FIG. 4 wherein the packaged tool is improperly installed to the surgical device, and wherein the one or more controllers compares the expected tool center point from FIG. 4 to an actual state of the tool center point to determine an error condition.

DETAILED DESCRIPTION

Described herein are trackable protective packages for tools, and systems and methods for tracking the protective packaging for various purposes, such as to confirm installation of the tool to a surgical device.

A. Examples of Protective Packaging for Tools

Figure 1:
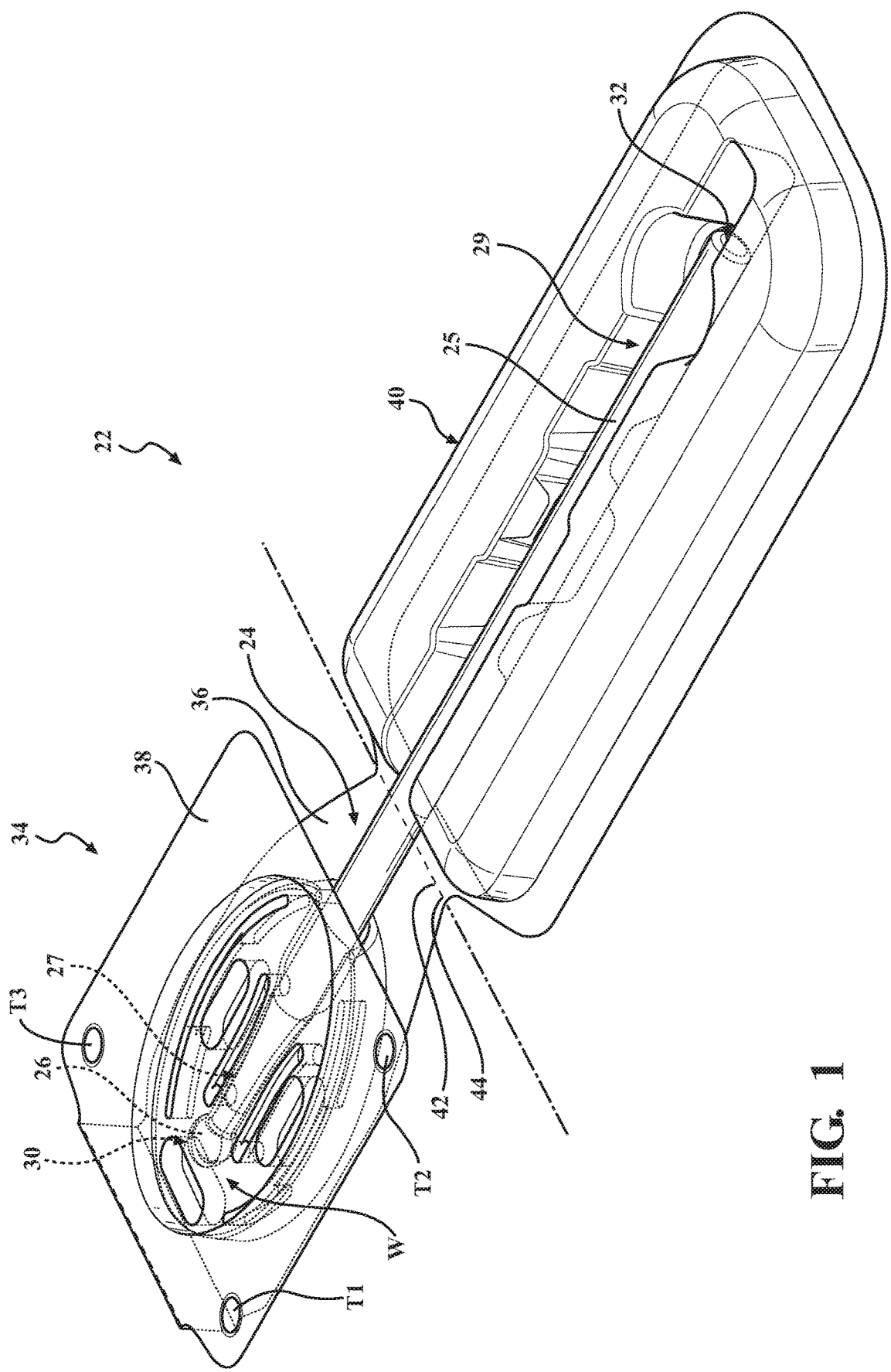
FIG. 1 is a perspective view of a protective packaging for retaining a tool in accordance with one example.

Referring to FIG. 1, a non-limiting example of a protective packaging 22 is illustrated. The protective packaging 22 is specifically shaped to accommodate and retain a tool 24 and provides safe, sterile and secure handling of the tool 24 during storage, transport, and mounting of the tool 24 on a surgical device 28 (see FIGS. 3 and 5). In view of the techniques described below, having the protective packaging 22 be utilized during or after mounting of the tool 24 on the surgical device 28 provides significant advantages.

The protective packaging 22 and its uses during tool 24 installation can be like those described in US Pat. App. Pub. No. 2018/0296297A1, entitled "Packaging Systems and Methods for Mounting A Tool on A Surgical Device", the disclosure of which is hereby incorporated by reference in its entirety. However, the protective packaging 22 can have different configurations from the protective packaging 22 shown.

In one example, the tool 24 is a device that is configured to remove material from a target site, such as a bone of a patient, soft tissue, or the like. For these reasons, the tool 24 is likely to be a sharp object. The tool 24 can also be a passive object, i.e., a purely mechanical object having no actively energizable electrical components. Examples of tools 24 include, but are not limited to burs, drill bits, screw drivers, saws, and the like.

The tool 24 comprises a working portion W or energy applicator. The working portion W is a feature of the tool 24 that is configured to interact with and manipulate the target site. When the tool 24 is a bur, the working portion W is the bur head 26 rigidly coupled to a tool shaft 25 (as shown). When the tool 24 is a drill bit, the working portion W can be the threaded portion of the drill shaft or a distal tip of the drill bit. When the tool 24 is a saw, the working portion W can be a distal tip or teeth of the saw blade. For simplicity in description, the tool 24 described in the examples below is a bur and the working portion is the bur head 26. However, various other tools 24 with different working portions W are fully contemplated to be utilized with the techniques described herein.

The surgical device 28 may be any apparatus configured to receive and operate the tool 24. In other words, the surgical device 28 may provide actuation, control, power, etc., to the tool 24. The surgical device 28 of FIGS. 3-5 is a surgical robot R having an end effector configured to receive the tool 24. In this example, the surgical device 28 can be the robot R and/or the end effector. Other example combinations of the tool 24 and the surgical device 28 are contemplated. For example, possible combinations may include: a saw or a blade configured to be received by a saw driver; a router, a curved bur, or a sleeve connector for a bur configured to be received by a handheld rotary instrument; electrodes configured to be received by a smoke evacuation pencil; a scalpel configured to be received by a scalpel handle; an ultrasonic tip configured to be received by an ultrasonic aspirator; and an endoscopic shaver or cutter configured to be received by an endo-handpiece. For any of the example above, the surgical device 28 can be a hand-held instrument configured to be supported (against the force of gravity) and manually moveable in space by the hand and arm of a user. It is to be understood that other surgical devices for receiving tools are contemplated. As will be described below, the tool 24 and/or surgical device 28 according to any configuration may be tracked by a navigation system.

In one example, the tool 24 includes a distal region 27 and an attachment portion 29. The working portion W is at the distal region 27 of the tool 24 and the attachment portion 29 is the part of the tool 24 that installs to the surgical device 28. In some instances, the attachment portion 29 is located a proximal region of the tool 24, opposite the distal region 27. At the distal region 27 is a distal end 30 and at the attachment region 29 is a proximal end 32 of the tool 24. A length of the tool 24 can be defined between the distal end 30 and the proximal end 32. If the tool 24 is symmetrical about an axis of rotation, a tool axis may be defined between the distal end 30 and the proximal end 32.

In this example, the protective packaging 22 provides a casing that comprises a distal section 34 that has a cavity to retain the distal region 27 of the tool 24 to protect the operator and prevent contamination. The distal section 34 may comprise distal portions 36, 38 that collectively retain the tool 24. The distal portions 36, 38 can be separate components or can be integrally formed as one component. The distal portions 36, 38 may be pivotably coupled to one another such that they can open and close, in a clamshell configuration. In such examples, the distal section 34 can be opened to enable removal of the tool 24 from the protective packaging 22 and closed to enable retention of the 24 in the protective packaging 22. In other examples, the distal portions 36, 38 can be permanently coupled together, such as by using a high frequency weld, adhesive, integrally formed material, etc. In such examples, the protective packaging 22 can be configured to slide over and off the tool 24.

In some examples, the protective packaging 22 can have only the distal section 34. In other examples, such as that shown in FIG. 1, the protective packaging 22 can optionally include a proximal section 40 that couples to the distal section 34. The proximal section 40 can be provided with a cavity to retain the proximal end of the tool 24, such as the tool shaft 25. The proximal section 40 can be pivotably coupled to the distal section 34 at a hinge 42. This hinge 42 enables the proximal section 40 to be detached from the tool shaft 25 simultaneously while remaining hinged to the distal section 34. This way, the tool shaft 25 can be exposed for installation while the proximal section 40 can provide shielding protection for the operator's hand. In other examples, the hinge may comprise a perforation 44 that enables the proximal section 40 to be detached completely from the distal section 34.

Importantly, the protective packaging 22 provides a low dimensional tolerance and/or tight mechanical fit when retaining the tool 24. Features may be designed into the tool 24 and/or the protective packaging 22 to achieve the fit. For example, a hole could be placed in a saw blade with a mating protrusion in the protective packaging 22, or an undercut could of a drill shaft could be used to align with a protrusion in the protective packaging 22. As will be described below, the tight tolerance securely retains the tool 24 while providing a known relationship between features of the protective packaging 22 (e.g., trackable features) and the tool 24. In one example, the dimensional tolerance is less than 1 mm or even less than 0.1 mm. Any suitable casing of the protective packaging 22 is contemplated that protect the operator and prevent contamination while maintaining a tight mechanical retention of the tool 24. Hence, the casing of the protective packing 22 is not limited to the examples described herein.

The protective packaging 22 may comprise, in part or entirely, material such as polyethylene terephthalate glycol-modified (PETG). Other suitable materials may include, without limitation, polymers such as polyethylene terephthalate (PET), high-density polyethylene (HDPE), polyvinyl chloride (PVC), low-density polyethylene (LDPE), polypropylene (PP), and polystyrene (PS), epoxy and other resins, and malleable metals such as aluminum. The protective packaging 22 can be formed by thermoforming, injection molding, vacuum molding, blow molding, or other manufacturing processes.

Various different configurations of the protective packaging 22 are contemplated. For example, the protective packaging 22 can be hermetically sealed (against liquid and gas). The protective packaging 22 can be reusable (sterilizable) or disposable (single use). The protective packaging 22 can have features, such as texturized features, to enable the operator to easily grip the protective packaging 22 for tool 24 installation or to open and close the distal portions 36, 38.

The protective packaging 22 or any of its components can be adjustable in size or dimension, and can be elastic, flexible, or deformable. The protective packaging 22 can be tool 24 specific or generically usable for different tools. As will be described below, the protective packaging 22 can also have features that enable the protective packaging 22 to be detectable and/or to avoid being detectable.

The protective packaging 22 can be used for initial attachment of the tool 24 to the surgical device 28 or it can be used for re-attachment of the tool 24 during the surgical procedure. There may be a need to re-check the position of the tool 24 during the procedure or the tool 24 may be removed for a portion of the procedure and later re-installed. The protective packaging 22 can have any combination of the features described herein and can have configurations or features other than those described herein.

B. Trackable Features for the Protective Packaging

Figure 2:
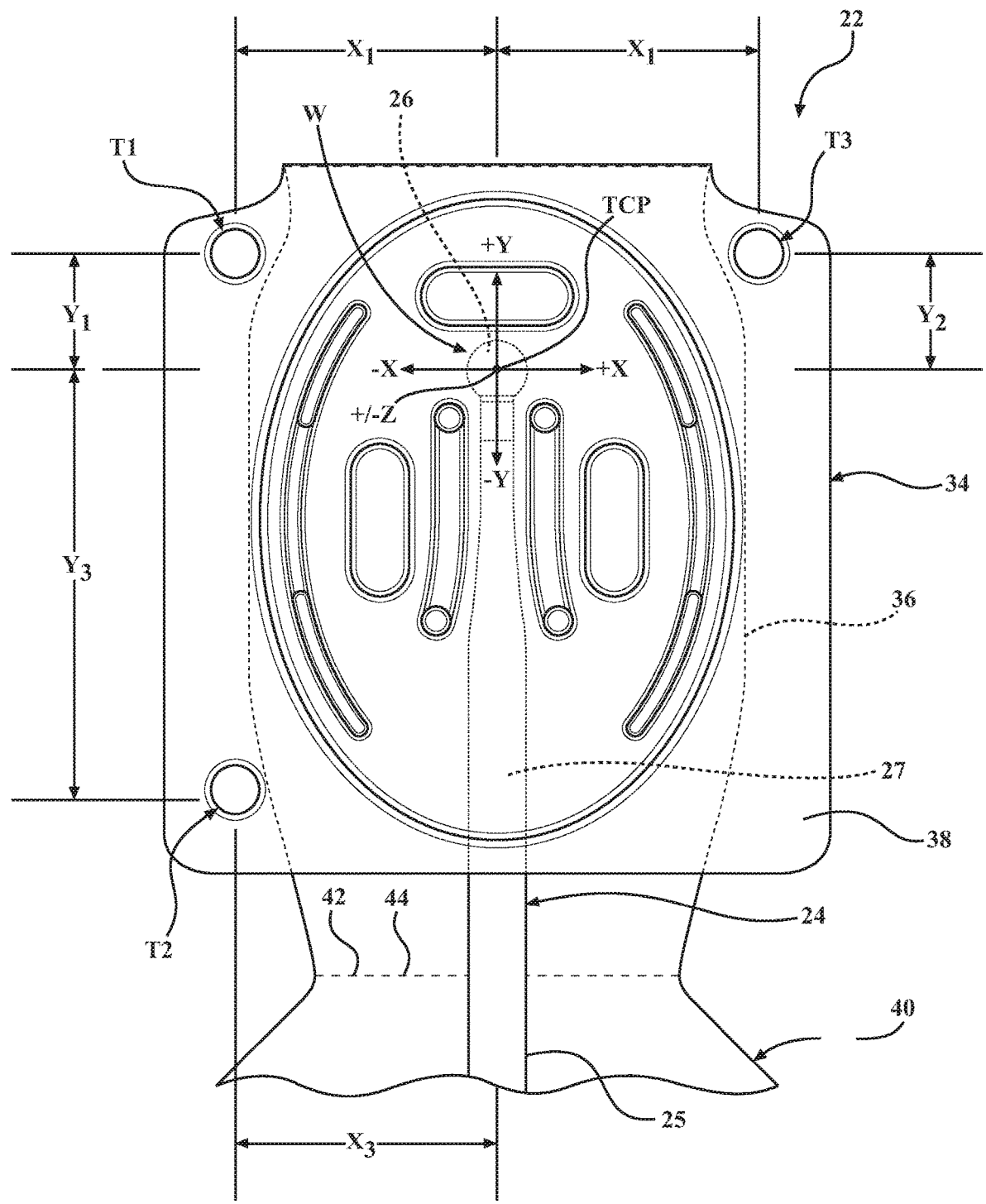
FIG. 2 is a plan view of the protective packaging of FIG. 1 further illustrating trackable features on the packaging and their relationship to a tool center point of the tool.

As shown in the non-limiting example of FIGS. 1 and 2, the protective packaging 22 can comprise one or more trackable features T. The trackable features T can be utilized to track the tool 24 when the tool 24 is retained by the protective packaging 22. The trackable features T can also be utilized to track the protective packaging 22 when the tool 24 is not retained therein. In another example, described below, the trackable features T are utilized to determine whether or not the tool 24 is properly mounted/installed to the surgical device 28.

The protective packaging 22 may comprise any number and any configuration of trackable features T. In this example, three trackable features T1-T3 are provided with the protective packaging 22. Having at least three trackable features T provides the ability to know the position and orientation of the protective packaging 22. The trackable features T can be placed on or affixed to the protective packaging 22 utilizing any suitable technique. Alternatively, the trackable features T can be integrally formed on, in, or with the protective packaging 22. For example, the trackable features T can be embedded within the material of the protective packaging 22. The trackable features T can also be uniquely identifiable features integral to the protective packaging 22, such as edges, protrusions, recesses, shapes or any of the components of the protective packaging 22 described herein.

The trackable features T can be passive or actively energized and can be of any appropriative type of detectable configuration. The trackable features T may be infrared trackable features. When infrared, the trackable features T can be retroreflective elements or LED emitters, for example. Alternatively or additionally, the trackable features T can be passive landmarks, patterns, and/or shapes that are uniquely identifiable. The trackable features T can also be configured with patterns, colors, gradients, and/or texturized materials. In other examples, the trackable features T can be passive or active magnetic or electro-magnetic elements, passive or active radio frequency elements, radio-opaque elements, ultrasound detectable elements, or any combination of the above-described configurations.

The trackable features T can be provided on the protective packaging 22 in any location, manner, or configuration. For example, the trackable features T can be positioned the first and/or second distal portions 36, 38. The trackable features T can also be positioned on the proximal section 40. In one example, the trackable features T are provided only on the distal section 34, but not the proximal section 40. This configuration is based on the practical consideration that the working portion W of the tool 24 will remain retained by the distal section 34 during tool 24 installation, whereas the proximal section 40 may be detached from the protective packaging 22 or otherwise pivoted relative to the distal section 34 prior to installation. Furthermore, the trackable features T can be positioned on one side or multiple sides of the protective packaging 22, including any of the top, bottom, or left or right sides, as needed, to enable the trackable features T to be detectable.

In another example, each of the first and second distal portions 36, 38 comprises an exterior surface, which is exposed when the protective packaging 22 is closed. In this example, one or more trackable features T can be coupled to the exterior surface of at least one of the first and second distal portions 36, 38. As such, the trackable features T can be readily visible when the protective packaging 22 is closed.

In yet another example, the trackable features T may comprise sub-components on different parts of the protective packaging 22. For example, each of the first and second distal portions 36, 38 comprises an interior surface. The interior surfaces engage each other when the protective packaging 22 is closed. In this example, one or more trackable features T comprise a first component coupled to the interior surface of the first distal portion 36 and a second component coupled to the interior surface of the second distal portion 38. The first and second components are positioned such that when the protective packaging 22 is closed, the first and second components engage or combine to form the trackable feature T. In other words, the trackable feature T may be functional when the protective packaging 22 is fully closed and non-functional when the protective packaging 22 is partially or entirely open. The first and second components can be electrical, magnetic, or layers of material (e.g., reflective material) that work together to form the trackable feature T when the protective packaging 22 is closed. The trackable features T can also extend through the material of the protective packaging 22 such that the trackable feature T is on both the exterior and interior surfaces of the protective packaging 22.

The protective packaging 22 may comprise a material that is transparent to light. The transparent material can increase visibility and/or reduce retro-reflectivity of the protective packaging 22 to increase accuracy in detecting the trackable features T. When transparent, visible light penetration through the protective packaging 22 material may be greater than 75%, 90%, or 95%. The protective packaging 22 can also be equipped with surface properties or features to reduce retro-reflectivity. Examples of such properties or features include, but are not limited to, rough surfaces, dimpled surfaces, anti-reflective coating or film, or the like.

The trackable features T and the configuration of the protective packaging 22 can be different than the examples described above.

C. Example Navigation Systems

To implement tracking of the trackable features T, a navigation system 100 is provided, as shown in FIG. 3, for example. The navigation system 100 can be utilized in conjunction with the surgical device 28. As shown in FIG. 3, for example, the surgical device 28 is the end effector of the robot R that is configured to receive the tool 24.

The navigation system 100 is configured to track movement of various objects. Such objects include, for example, the protective packaging 22, the robot R, the surgical device 28 and the anatomy of a patient. The navigation system 100 tracks these objects with respect to a (navigation) localizer coordinate system LCLZ. Coordinates in the localizer coordinate system LCLZ may be transformed to the robot (manipulator) coordinate system MNPL, and/or vice-versa, using transformation techniques described herein.

One example of the navigation system 100, surgical robot, control techniques, and transformations associated therewith, which can be utilized with the techniques herein, is described in U.S. Pat. App. Pub. No. 2018/0168750A1 filed on Dec. 13, 2017, entitled, "Techniques for modifying tool operation in a surgical robotic system based on comparing actual and commanded states of the tool relative to a surgical site," the entire disclosure of which is hereby incorporated by reference.

The navigation system 100 may include a cart assembly 102 that houses the one or more controllers 104, such as a navigation computer, and/or other types of control units. The one or more controllers 104 may also be located in the surgical device 28 and/or a cart of the robot R. The one or more controllers 104 may be located in components or subsystems other than that shown in FIG. 3 and may be implemented on any suitable device or devices in the system 100 other than the configuration shown. In one example, the controllers for the navigation system and the robot are two different controllers performing different operations, and can be configured, for example, as described in U.S. Pat. App. Pub. No. 2018/0168750A1. The one or more controllers 104 can comprise software and/or hardware configured to perform all the tasks described herein. Example of hardware may comprise processors, CPUs, microprocessors, integrated circuits, non-transitory memory, graphic processing units, hard drives, and input/output devices.

A navigation interface is in operative communication with the one or more controllers 104. The navigation interface includes one or more displays 106. The one or more controllers 104 is capable of displaying graphical (actual or virtual) representations of the relative states of the tracked objects to the operator using the one or more displays 106. As will be described below, alerts, notifications, or error messages can also be represented on one or more of the displays 106.

In addition to the trackable features T described with respect to the protective packaging 22, the other objects tracked by the navigation system 100 include one or more trackers or trackable features. In one example, as shown, the trackers may include a tool tracker 108 attached to surgical device 28 (e.g., end effector), a robot tracker 109 attached to the base of the robot R (as shown) or to one or more links of the robot R, and target site trackers (not shown), which can be attached to a patient. Any one or more of the trackers may include active or passive trackable features, and may be used with any tracking modality described herein.

The navigation system 100 also includes a navigation localizer 110 (hereinafter "localizer") that tracks a state of trackable features T on the protective packaging 22, and other trackers or trackable features. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like. The localizer 110 provides the state of these tracked objects to the one or more controllers 104 to enable the one or more controllers 104 to make determinations based on such information.

In one example, as shown in FIG. 3, the localizer 110 is an optical localizer and includes a camera unit 112 with one or more optical sensors 114. The localizer 110 can be an infrared based localizer suitable for detecting trackable features T that are configured with active or passive infrared elements. Although one embodiment of the navigation system 100 is shown in FIG. 3, the navigation system 100 may have any other suitable configuration for tracking the trackable features T.

Additionally, or alternatively, the localizer 110 can be a machine vision system, The machine vision system can comprise a camera that is configured to detect trackable features T that can include patterns, shapes, colors, textures, gradients and/or uniquely identifiable features provided by the protective packaging 22. The machine vision system can employ various types of imaging and imaging processing modalities, such as 2D/3D visible light imaging, depth maps, pixel analysis, edge detection, pattern recognition, and the like. One example of a machine vision system that can be utilized is described in US Publication No. 2017/0143432A1, entitled, Systems and Methods for Establishing Virtual Constraint Boundaries," the entire contents of which are incorporated by reference herein.

In another example, the navigation system 100 and/or localizer 110 are radio frequency (RF)-based. For example, the navigation system 100 may comprise an RF transceiver in communication with the one or more controllers 104. The trackable features T of the protective packaging 22 may comprise RF emitters or transponders. The RF emitters or transponders may be passive or actively energized. The RF transceiver transmits an RF tracking signal and generates state signals to the one or more controllers 104 based on RF signals received from the RF emitters. The one or more controllers 104 may analyze the received RF signals to associate relative states thereto. The RF signals may be of any suitable frequency. The RF transceiver may be positioned at any suitable location to effectively track the objects using RF signals. Furthermore, the RF emitters or transponders may have any suitable structural configuration that may be much different than the trackers or trackable features as shown in the Figures.

The navigation system 100 and/or localizer 110 can also be electromagnetically based. For example, the navigation system 100 may comprise an EM transceiver coupled to the one or more controllers 104. The trackable features T of the protective packaging 22 may comprise EM components, such as any suitable magnetic tracker, electro-magnetic tracker, inductive tracker, or the like. The trackable features T may be passive or actively energized. The EM transceiver generates an EM field and generates state signals to the one or more controllers 104 based upon EM signals received from the trackers. The one or more controllers 104 may analyze the received EM signals to associate relative states thereto. Again, such navigation system 100 embodiments may have structural configurations that are different than the navigation system 100 configuration as shown throughout the Figures.

In another example, the navigation system 100 and/or localizer 110 are ultrasound-based. For example, the navigation system 100 may comprise an ultrasound imaging device coupled to the one or more controllers 104. The ultrasound imaging device images any of the aforementioned objects, e.g., the protective packaging 22 and/or trackable features T generate state signals to the one or more controllers 104 based on the ultrasound images. For example, the ultrasound imaging device may be a portable device whose position is tracked. The portable device can be positioned proximate to any object to track the object. The one or more controllers 104 may process the images in near real-time to determine states of the objects. The ultrasound imaging device may have any suitable configuration and may be different than the camera unit 112 as shown in FIG. 3.

The navigation system 100 and/or localizer 110 may be based on any combination of the tracking modalities above and may have any other suitable components or structure not specifically recited herein. Furthermore, any of the techniques, methods, and/or components described above with respect to the camera-based navigation system 100 shown throughout the Figures may be implemented or provided for any of the other embodiments of the navigation system 100 described herein.

D. Tool Center Point and Relationship to Protective Packaging

According to the techniques described herein, the trackable features T of the protective packaging 22 are utilized to track the tool 24 when the tool 24 is retained by the protective packaging 22. More specifically, the navigation system 100 can track the trackable features T to determine whether or not the tool 24 is properly mounted/attached to the surgical device 28.

To help facilitate this technique, the protective packaging 22 provides a low dimensional tolerance and tight mechanical fit when retaining the tool 24. Furthermore, the protective packaging 22 is involved with the process of installing the tool 24 to the surgical device 28. Therefore, tracking the protective packaging 22 to determine whether or not the tool 24 is properly mounted/attached to the surgical device 28 provides the advantages of reducing steps and reducing additional devices in the operating room. Furthermore, the tight tolerance provides measurements with a high degree of accuracy as compared with prior techniques. The tight tolerance provided by the protective packaging 22 enables the techniques herein to treat the protective packaging 22 as a virtual extension of the tool 24 geometry for calibration or verification purposes. By providing tracking features on the protective packaging 22, permanent tracking features on the tool 24 (particularly near the working portion) can be avoided. Avoiding permanent tracking features on the tool 24 is advantageous since permanent tracking features on a tool 24 can interfere with tool 24 operation or with the surgical site and cannot be located proximate enough to working portion of the tool 24 since the working portion is utilized to manipulate the anatomy. On the other hand, the protective packaging 22 is installed on the working portion, and hence, maximizes the calibration and verification measurement capability to the distal-most portion of the tool 24. Furthermore, the methods described herein provide a seamless user experience, as accuracy checks can be done without adding external components or steps.

Referring to FIG. 2, the tool 24 comprises a tool center point (TCP), which in one embodiment, is a predetermined reference point defined at the working portion W or relative to the working portion W. In one embodiment, the TCP is assumed to be located at the center of a spherical of the tool 24 such that only one point is tracked. The TCP may relate to a bur having a specified diameter. Often, the TCP is defined at a location that is at a center of the working portion W. For example, as shown in FIG. 2, the TCP is located at the spherical center of the bur. However, this may not always be the case. For example, the TCP of a drill bit can be a point in the cylindrical center of the drill, but located anywhere along the tool shaft 25. Similarly, for a saw blade, the TCP can be located anywhere on the saw blade. The TCP can also be arbitrarily defined somewhere with respect to the working portion W. Therefore, the term "center" is not limited to the geometrical center of the working portion W. The TCP may be defined according to various manners depending on the configuration of the working portion W.

Furthermore, the TCP can be a physical point on the working portion W or the TCP can be a virtual point. In either instance, the one or more controllers 104 is configured to store the predetermined TCP state relative to known geometry for the specified tool 24. Aside from the techniques described herein for confirming installation of the tool 24, the TCP can also be utilized by the one or more controllers 104 to facilitate control of the tool 24 and/or surgical device 28. For example, such control can be movement of the tool 24 relative to virtual boundaries or tool paths. Examples of TCPs and uses thereof in controlling surgical devices can be like those described in US Pat. App. Pub. No. 2018/0168750A1, entitled "Techniques for modifying tool operation in a surgical robotic system based on comparing actual and commanded states of the tool relative to a surgical site," the entire contents of which are hereby incorporated by reference.

In instances where the tool 24 is not directly tracked by the navigation system 100, the state of the working portion W relative to the surgical device 28 or relative to the navigation system 100 may not be known. Advantageously, when the tool 24 is retained by the protective packaging 22, the actual state of the TCP can be determined since the protective packaging 22 has trackable features T. As used herein, the "actual" state of the TCP is the real position and/or orientation of the TCP in physical 3D space or in a global coordinate system. In one example, this global coordinate system is the localizer coordinate system LCLZ. To facilitate this determination, the trackable features T are specifically positioned on the protective packaging 22 with a predetermined state defined relative to the actual state of the TCP. The one or more controllers 104 is configured to store these predetermined states of the trackable features T relative to the actual state of the TCP for further evaluations, as will be described below.

Prior to tracking, the actual state of the TCP can be assumed in the correct state relative to the trackable features T based on the understanding that the tool 24 is properly retained by the protective packaging 22. Mainly, the various features of the protective packaging 22 described above (e.g., tight mechanical fit) help to ensure that the tool 24 is properly retained relative to the protective packaging 22 so as to validate this assumption.

As shown in the example in FIG. 2, the trackable features T1-T3 (in this case, passive markers) and the actual state of the TCP can be defined in a common coordinate system (e.g., the coordinate system of the protective packaging 22). In this example, the actual state of the TCP can be considered the origin of the coordinate system, and the center of each trackable feature T is utilized for the coordinate measurements. However, it is not necessary to define the actual state of the TCP at the origin of the coordinate system nor to utilize the center of each trackable feature T for measurement.

In FIG. 2, an X-axis and Y-axis define the coordinate system, where X and Y are distances relative to the origin TCP. There may also be Z-axis coordinates (in and out of the page of FIG. 2) that can be considered in this coordinate system. Z-axis coordinates would be appropriate if any of the trackable features T are defined on a different plane relative to the actual state of the TCP or relative to each other. For simplicity in description and illustration, the Z-axis coordinates are omitted on the assumption that the trackable features T are coplanar with the actual state of the TCP. However, the manner in which the Z-axis coordinates are determined can be like that described herein relative to the X and Y-axis coordinates.

Here, trackable feature T1 is defined at −X1, Y1 relative to the actual state of the TCP, trackable feature T2 is defined at −X1, −Y3 relative to the actual state of the TCP, and trackable feature T3 is defined at X1, Y2, relative to the actual state of the TCP. The coordinate measurements and trackable feature T placement relative to the actual state of the TCP in FIG. 2 is only one example. Of course, the trackable features T can have other predetermined states relative to the actual state of the TCP depending on factors such as the nature of the TCP, the types and positions of the trackable features T, and the structure of the protective packaging 22, etc.

E. Techniques for Evaluating Tool Installation with Tracked Packaging

Referring back to FIG. 3, the navigation system 100 is shown with the tool 24 coupled to the surgical device 28. The operator installs the tool 24 to the surgical device 28 by holding the protective packaging 22. In this example, it is assumed that an attempt was made to install the tool 24 to the surgical device 28, however, the operator may not be aware whether the tool 24 is properly installed.

As can be understood from the example of FIG. 2, the state of the actual TCP is known relative to the states of the trackable features T. As will be described below, the trackable features T of the protective packaging 22 and this known relationship are utilized by the navigation system 100 and one or more controllers 104 for determining whether the tool 24 is properly mounted/installed to the surgical device 28.

To facilitate this determination, the navigation system 100 is shown with various transforms (T) for determining the actual state of the TCP in a global coordinate system, e.g. LCLZ. The transform (T), when calculated, gives the state (position and/or orientation) of a first component in its respective coordinate system relative to the state of a second component in its respective coordinate system. The one or more controllers 104 calculates/obtains and combines a plurality of transforms (T) from the various components of the system, e.g., for purposes such as to validate installation of the tool 24 and/or to control the surgical device 28 or robot R when the tool 24 is installed. The transforms (T) are computational determinations but are represented in FIG. 3 by arrows between the subject components for illustrative purposes. The directionality of the arrow head is not intended to limit the direction of the transform. In other words, the transform (T) can give the state of one component with respect to the other, or vice versa.

In one embodiment, each transform (T) is specified as a transformation matrix, such as a 4×4 homogenous transformation matrix. The transformation matrix, for example, includes three unit vectors representing orientation, specifying the axes (X, Y, Z) from a first coordinate system expressed in coordinates of a second coordinate system (forming a rotation matrix), and one vector (position vector) representing position using the origin from the first coordinate system expressed in coordinates of the second coordinate system.

Example systems and methods for obtaining and computing transforms of the various components of the system is explained in U.S. Pat. No. 9,119,655, entitled, "Surgical Manipulator Capable of Controlling a Surgical Instrument in Multiple Modes," and U.S. Pat. App. Pub. No. 2018/0168750A1 filed on Dec. 13, 2017, entitled, "Techniques for modifying tool operation in a surgical robotic system based on comparing actual and commanded states of the tool relative to a surgical site," the entire disclosures of which are hereby incorporated by reference.

As shown in FIG. 3, the transforms include a first transform (T1) between the localizer 110 and trackable features T of the protective packaging 22 and a second transform (T2) (best shown in FIG. 3A) between the trackable features T and the actual state of the TCP. Other transforms that may be utilized include a third transform (T3) between the localizer 110 and the surgical device 28 tracker 108, a fourth transform (T4) between the surgical device 28 tracker 108 and a reference point on the surgical device 28, a fifth transform (T5) between the actual state of the TCP and the reference point on the surgical device 28, and/or a sixth transform (T6) between the reference point on the surgical device 28 and a base of the robot (R).

Transforms (T1) and (T3) are obtained using tracking data from the localizer 110. In other words, the localizer 110 tracks the state of the trackable features T of the protective packaging 22 and the state of the surgical device 28 tracker 108 relative to the LCLZ coordinate system. Transform (T2) is obtained based on the known relationship between the trackable features T of the protective packaging 22 and the actual state of the TCP of the tool 24 retained by the protective packaging 22, as described in the prior section. Transform (T4) is obtained based on a known relationship between the surgical device 28 tracker 108 and the reference point on the surgical device 28. Transform (T5) is obtained based on a known relationship between an expected state of the TCP (i.e., the state of the TCP when the tool 24 is installed properly, which will be described further below) and the reference point on the surgical device 28. Transform (T6) can be determined based on kinematic data of the robot (R) stored by the one or more controllers 104 without intervention from the navigation system 100. Alternatively or additionally, transform (T7) can be obtained by localizer 110 determining the relationship between the surgical device 28 tracker 108 and the tracker 109 at the base of the robot R. Not all of these transforms (T) may be utilized in every instance, and these transforms (T) can be utilized in various combinations.

Any known relationship data (e.g., for transforms T2, T4 or T5) is stored by the one or more controllers 104 and may be fixed (constant or static) or variable. In embodiments where the known relationship data is fixed, the known relationship data may be derived from calibration information relating to the respective components (e.g., the surgical device 28, the surgical device 28 tracker 108, and the expected state of the TCP). For example, the calibration information may be obtained at a manufacturing/assembly stage, e.g., using coordinate measuring machine (CMM) measurements, etc. The known relationship data may be obtained using any suitable method, such as reading the known relationship data from a computer-readable medium, an RFID tag, a barcode scanner, or the like. The known relationship data may be imported into system 100 at any suitable moment such that the known relationship data is readily accessible by the one or more controllers 104. In embodiments where the known relationship data is variable, the known relationship data may be measured or computed using any ancillary measurement system or components, such as additional sensors, trackers, encoders, or the like. The known relationship data may also be acquired after mounting the surgical device 28 tracker 108 to the surgical device 28 in preparation for a procedure by using any suitable technique or calibration method.

With reference to FIGS. 4 and 5, the one or more controllers 104 is configured to evaluate the information described above to determine whether the tool 24 is properly mounted to the surgical device 28. For example, the one or more controllers 104 can determine whether or not the TCP is in the proper position and take action in response.

In FIG. 4, the one or more controllers 104 is configured to store the expected state of the TCP based on an expected condition in which the tool 24' is properly mounted to the surgical device 28. The expected state of the TCP is a virtual state (e.g., point) stored in one or more controllers 104 memory rather than a physical state on the tool 24 itself. For this reason, a dotted representation of the tool 24' is shown in FIG. 4 to represent the expected state of the TCP during an assumed proper installation. Furthermore, in FIG. 4, a proper installation line 120 is shown within the tool receiving portion of the surgical device 28 to illustrate one example of where a proximal end 32 of the tool 24 should be relative to the surgical device 28 when the tool 24' is properly installed. In this illustration, the hypothetical tool 24' is fully seated within the surgical device 28 (and hence properly installed) such that the proximal end 32 of the tool 24' aligns with line 120.

This installation representation is for simplicity in description and illustration, and tool 24' installation schemes will vary depending on the type of tool being installed and the configuration of the surgical device 28. Hence, the use of an "installation line" 120 is not intended to limit the nature of proper installation conditions. Indeed, the proper installation between the tool 24 and the surgical device 28 may be defined by any suitable number of reference datum having any complexity designated by the respective installation scheme. Additionally, or alternatively, proper installation may be defined by any suitable physical parameter measured between the tool 24 and the surgical device 28, wherein the physical parameter can be correlated with, compared to, or otherwise associated to physical parameters derivable from the trackable features of the packaging 22 and the TCP. Such physical parameters may include, but not limited to: position, magnitude of displacement, distance, orientation, linear motion or velocity, angular motion or velocity, inertial parameters, force parameters, displacement parameters, pressure parameters, torque parameters. Hence, instead of comparing the expected state of the TCP to the actual state of TCP based on static position, the techniques may be utilized to compare an expected motion of the TCP during expected proper installation to actual motion of the TCP during actual installation. Accordingly, the term "state" is not intended to be limited to a static moment in time, but may encompass a period of time. Hence, the term "state" can be static or dynamic.

Furthermore, the installation scheme between the tool 24 and the surgical device 28 may include any suitable sensing devices, including but not limited to, direct (DC) electrical connection sensors, proximity sensors, hall effect sensors, electromagnetic sensors, radio frequency sensors, inductive sensors, capacitive sensors, and the like. These sensors are not intended to replace the techniques described herein, but rather can optionally be utilized in conjunction with the techniques described herein, for purposes such as tool identification, coarse tool installation, or tool presence detection.

The expected state of the TCP can be locally derived from the described known relationship data for transform T5, which can obtained using any manner described above. Additionally, or alternatively, the expected state of the TCP can be based on separate known relationship data obtained about the relationship between the expected state of the TCP and any other portion of the surgical device 28, such as the portion that receives the tool 24. For any given pose of the robot R or state of the surgical device 28, the one or more controllers 104 can determine the expected state of the TCP based on combining the transforms (T) described above. For example, the expected state of the TCP can be determined by combining any one of the following combinations: (T3+T4+T5), (T5+T6), (T5+T6+T7), etc.

If/when the tool 24 is properly installed, the expected TCP and the actual TCP states should be identical. Otherwise, if the tool 24 is improperly installed, the expected TCP and the actual TCP states will be different. Additionally, the trackable features may be different for different tools 24. This will allow the system to further identify the tool 24 being used and/or confirm the correct tool is used.

FIG. 5 illustrates the actual installation condition of the tool 24 relative to the surgical device 28. In this situation, the tool 24 is improperly mounted to the surgical device. This error condition is illustrated by distance d between the proximal end 32 of the tool 24 and the proper installation line 120. In other words, the tool 24 is not fully seated in the surgical device 28. The distance d can be difficult to detect to the human eye, e.g., 1 mm or less. Hence, the tool 24 is not properly installed, but may appear so to the operator. Although the error condition is represented by distance d in this example, it is possible that the error condition can take other forms depending on the nature of the tool 24, the surgical device 28, and/or manner of installation. For example, the error condition can be an identification of an incorrect tool, improper rotation, linear position, orientation, damage to the tool, or any combination thereof. Regardless of the nature of the error condition, the techniques described herein are configured to detect the error.

Since the tool 24 is improperly installed in FIG. 5, the state of the actual TCP differs from the state of the expected TCP. In this example, the error condition (distance d) at the proximal end 32 of the tool 24 causes a corresponding gap d between the actual TCP and expected TCP states. Of course, other error conditions are possible. For example, a measured distance of the tool 24 that is offset with the tool insertion axis could indicate the tool 24 is damaged or is the incorrect tool.

The one or more controllers 104 can make this determination by obtaining the state of the actual TCP using the transforms (T) described above. Regardless of the pose of the robot R or the state of the surgical device 28, the one or more controllers 104 can determine the actual TCP state based on combining transformations (T1+T2). In other words, the actual state of the TCP is known to the one or more controllers 104 by the tracked state of the trackable features T of the protective packaging 22 and the predetermined states of the trackable features (T) defined relative to the actual state of the TCP. The one or more controllers 104 can arrive at the actual and expected TCP states by combining other combinations of transformations other than those specifically described.

Knowing the states of the actual and expected TCPs, the one or more controllers 104 can compare them using any suitable method, such as comparing position/orientation matrix data from the transforms, etc. In certain examples, different transformation combinations can be compared to validate comparison results. For example, the state of the actual TCP can be validated in the LCLZ coordinate system by comparing the tracking data of the surgical device 28 tracker 108 (transform T3) with the tracking data of the trackable features T on the protective packaging 22 (transform T1).

If the one or more controllers 104 determines that the states of the actual and expected TCPs, are different, the one or more controllers 104 may instruct generation of a notification or alert to inform the operator of the error condition. The alert or notification can be visual and provided on the display 106, as shown in FIG. 3. The alert can also be audible or haptic. Based on the nature of the error condition determined by the one or more controllers 104, the one or more controllers 104 can issue specific instructions about how to resolve the error condition given the circumstance. For example, the one or more controllers 104 may generate a notification instructing the operator to "fully insert the tool shaft" or "rotate the tool shaft 180 degrees clockwise". At any point, the one or more controllers 104 can re-assess the states of the actual and expected TCPs and inform the operator that the tool 24 is properly installed if the results of the comparison are favorable.

If the expected TCP state is different from the actual TCP state, the system may propose a decision process. For example the system may ask the user to confirm the correct tool is used, the system may suggest the user replace a damaged tool, and/or the user could instruct the system to accept the position of the actual state of the TCP and use the location for the remainder of the surgical procedure.

In certain instances, the one or more controllers 104 can be configured with a tolerance or threshold or range of error or acceptance when evaluating the differences between the states of the actual and expected TCPs. For instance, the one or more controllers 104 can have a tolerance of +/−0.1 mm such that if the states of the actual and expected TCPs are off by less than 0.1 mm, the one or more controllers 104 can nevertheless determine that the tool 24 is properly installed. The tolerance may be different from the value given, depending on many factors, such as the mechanical stack-up of components of the system, the nature of the installation, the accuracy of the localizer 110, or the like. If the actual state of the TCP falls within acceptable range of the expected state of the TCP tolerance, the state of the actual TCP can be stored by the one or more controllers 104 as the calibrated TCP state that will be used for controlling the surgical device 28.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method for operating a system comprising a surgical device and a tool for mounting to the surgical device, the tool including a working portion having a tool center point, a protective packaging for retaining the working portion, the protective packaging comprising trackable features having a predetermined state defined relative to an actual state of the tool center point, one or more controllers configured to store the predetermined states of the trackable features and to store an expected state of the tool center point based on an expected condition in which the tool is properly mounted to the surgical device, and a localizer, the method comprising:
  detecting, with the localizer, actual states of the trackable features in a coordinate system;
  determining, with the one or more controllers, the actual state of the tool center point in the coordinate system based on the actual states of the trackable features detected by the localizer and the predetermined state of the trackable features defined relative to the actual state of the tool center point;

comparing, with the one or more controllers, the actual state and expected state of the tool center point; and evaluating, with the one or more controllers, whether the tool is properly mounted to the surgical device based on comparing the actual state and expected state of the tool center point.

2. The method of claim 1, wherein the localizer is an infrared camera and at least one of the trackable features comprises a passive infrared element or active infrared element, and further comprising the infrared camera detecting the actual state of the at least one of the trackable features by detecting an infrared signal reflected by the passive infrared element or radiated by the active infrared element of the at least one of the trackable features.

3. The method of claim 1, wherein the localizer is a machine vision system and at least one of the trackable features comprises a predetermined pattern, shape or color, and further comprising the machine vision system detecting the actual state of the at least one of the trackable features by detecting the predetermined pattern, shape or color of the at least one of the trackable features.

4. The method of claim 1, further comprising the localizer tracking a state of the surgical device in the coordinate system and further comprising the one or more controllers determining the expected state of the tool center point in the coordinate system by combining the tracked state of the surgical device in the coordinate system and known relationship data between the expected state of the tool center point and a predetermined reference point on the surgical device.

5. The method of claim 1, further comprising the step of mounting the tool to the surgical device by grasping the protective packaging.

6. A method for operating a system comprising a surgical device and a tool for mounting to the surgical device, the tool including a working portion having a tool center point, a protective packaging for retaining the working portion, the protective packaging comprising trackable features having a predetermined state defined relative to an actual state of the tool center point, one or more controllers configured to store the predetermined states of the trackable features and to store an expected state of the tool center point based on an expected condition in which the tool is properly mounted to the surgical device, and a localizer, the method comprising:

detecting, with the localizer, actual states of the trackable features in a coordinate system;

determining, with the one or more controllers, the actual state of the tool center point in the coordinate system based on the actual states of the trackable features detected by the localizer and the predetermined state of the trackable features defined relative to the actual state of the tool center point;

comparing, with the one or more controllers, the actual state and expected state of the tool center point;

evaluating, with the one or more controllers, whether the tool is properly mounted to the surgical device based on comparing the actual state and expected state of the tool center point; and instructing, with the one or more controllers, generation of at least one of a haptic, audible, and visual alert in response to evaluating whether the tool is properly mounted to the surgical device.

7. A system comprising:
a surgical device;
a tool configured to mount to the surgical device and comprising a working portion having a tool center point;

a protective packaging configured to retain the working portion of the tool, the protective packaging comprising trackable features having a predetermined state defined relative to an actual state of the tool center point;

one or more controllers coupled to the surgical device and configured to store the predetermined states of the trackable features and to store an expected state of the tool center point based on an expected condition in which the tool is properly mounted to the surgical device; and a localizer coupled to the one or more controllers and being configured to detect actual states of the trackable features in a coordinate system;

and wherein the one or more controllers are configured to:
determine the actual state of the tool center point in the coordinate system based on the actual states of the trackable features detected by the localizer and the predetermined state of the trackable features defined relative to the actual state of the tool center point;

compare the actual state and expected state of the tool center point; and evaluate whether the tool is properly mounted to the surgical device based on comparing the actual state and expected state of the tool center point.

8. The system of claim 7 wherein the localizer is an infrared camera and at least one of the trackable features comprises a passive infrared element or active infrared element, and further comprising the infrared camera being configured to detect the actual state of the at least one of the trackable features by being configured to detect an infrared signal reflected by the passive infrared element or radiated by the active infrared element of the at least one of the trackable features.

9. The system of claim 7, wherein the localizer is a machine vision system and at least one of the trackable features comprises a predetermined pattern, shape or color, and further comprising the machine vision system being configured to detect the actual state of the at least one of the trackable features by being configured to detect the predetermined pattern, shape or color of the at least one of the trackable features.

10. The system of claim 7, wherein the localizer is further configured to track a state of the surgical device in the coordinate system and wherein the one or more controllers are further configured to determine the expected state of the tool center point in the coordinate system by combining the tracked state of the surgical device in the coordinate system and known relationship data between the expected state of the tool center point and a predetermined reference point on the surgical device.

11. The system of claim 7, wherein the protective packaging comprises:
a distal section defining a cavity configured to retain the working portion of the tool;
a proximal section coupled to the distal section and defining a cavity configured to receive an attachment portion of the tool, and wherein the proximal section is detachable from the distal section by a perforation; and
wherein the distal section comprises the trackable features.

12. A system comprising:
a surgical device;
a tool configured to mount to the surgical device and comprising a working portion having a tool center point;
a protective packaging configured to retain the working portion of the tool, the protective packaging comprising trackable features having a predetermined state defined relative to an actual state of the tool center point;

one or more controllers coupled to the surgical device and configured to store the predetermined states of the trackable features and to store an expected state of the tool center point based on an expected condition in which the tool is properly mounted to the surgical device; and a localizer coupled to the one or more controllers and being configured to detect actual states of the trackable features in a coordinate system;

and wherein the one or more controllers are configured to:
determine the actual state of the tool center point in the coordinate system based on the actual states of the trackable features detected by the localizer and the predetermined state of the trackable features defined relative to the actual state of the tool center point;

compare the actual state and expected state of the tool center point;

evaluate whether the tool is properly mounted to the surgical device based on comparing the actual state and expected state of the tool center point; and instruct generation of at least one of a haptic, audible, and visual alert in response to evaluating whether the tool is properly mounted to the surgical device.

* * * * *